(12) United States Patent
Jarsaillon et al.

(10) Patent No.: US 7,753,841 B2
(45) Date of Patent: Jul. 13, 2010

(54) GASTRIC RING FOR TREATMENT OF OBESITY

(75) Inventors: Philippe Jarsaillon, Roamme (FR); Michel Therin, Lyons (FR)

(73) Assignee: Sofradim Production, Trevoux (FR)

( * ) Notice: Subject to any disclaimer, the term of this patent is extended or adjusted under 35 U.S.C. 154(b) by 0 days.

(21) Appl. No.: 11/985,793

(22) Filed: Nov. 16, 2007

(65) Prior Publication Data

US 2008/0183196 A1 Jul. 31, 2008

Related U.S. Application Data

(63) Continuation of application No. 10/499,914, filed as application No. PCT/FR03/00038 on Jan. 8, 2003, now Pat. No. 7,297,103.

(30) Foreign Application Priority Data

Jan. 9, 2002 (FR) ................... 02 00260

(51) Int. Cl.
    *A61F 2/00* (2006.01)
(52) U.S. Cl. ...................................... 600/37
(58) Field of Classification Search .................. 600/30, 600/31, 37; 128/897, 899; 606/151, 153–155, 606/157
    See application file for complete search history.

(56) References Cited

U.S. PATENT DOCUMENTS

| | | | |
|---|---|---|---|
| 3,748,696 A | | 7/1973 | Martin |
| 4,592,339 A | * | 6/1986 | Kuzmak et al. ............. 128/899 |
| 6,596,004 B1 | * | 7/2003 | Regnault ..................... 606/157 |
| 6,685,620 B2 | | 2/2004 | Gifford, III et al. |
| 7,297,103 B2 | * | 11/2007 | Jarsaillon et al. ............. 600/37 |
| 2002/0095167 A1 | * | 7/2002 | Liddicoat et al. ............ 606/151 |

FOREIGN PATENT DOCUMENTS

| | | |
|---|---|---|
| EP | 0 61 1 561 | 8/1994 |
| FR | 2 612 392 | 9/1988 |
| WO | WO 00/41649 | 7/2000 |

\* cited by examiner

*Primary Examiner*—Charles A Marmor, II
*Assistant Examiner*—Christine D Hopkins
(74) *Attorney, Agent, or Firm*—Carter, DeLuca, Farrell & Schmidt, LLP

(57) ABSTRACT

A gastric ring includes a band that surrounds the wall of the stomach of a patient, and structure that makes it possible, after implantation, to modify the cross section of the opening delimited by the ring. The ring includes a band including at least one deformable zone made of a material that is elastically deformable in the longitudinal direction of the band, where the deformable zone has at least two bearing points formed therein at respective locations separated in the longitudinal direction of the band, and at least one rigid element made of a bioabsorbable or biodegradable material and bearing against the deformable zone in the area of the bearing points, where the rigid element, before absorption, maintains the bearing points at a distance from one another different than the distance separating the two bearing points in the absence of elastic deformation of the deformable zone of the band, and, upon absorption, no longer forms an obstacle to the return of the deformable zone of the band to its nondeformed state.

21 Claims, 1 Drawing Sheet

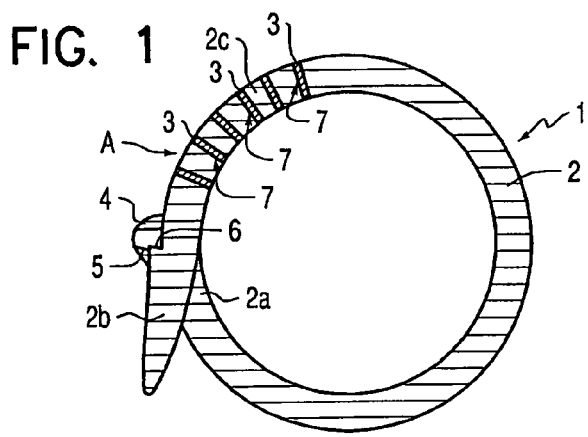
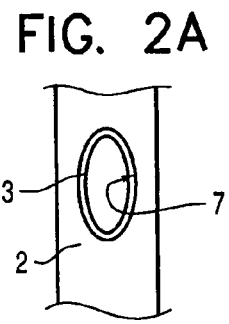
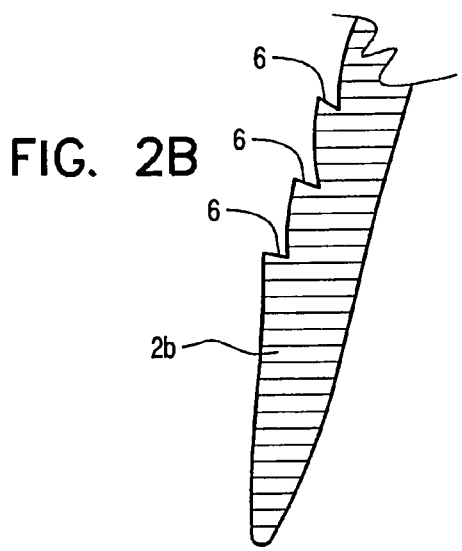
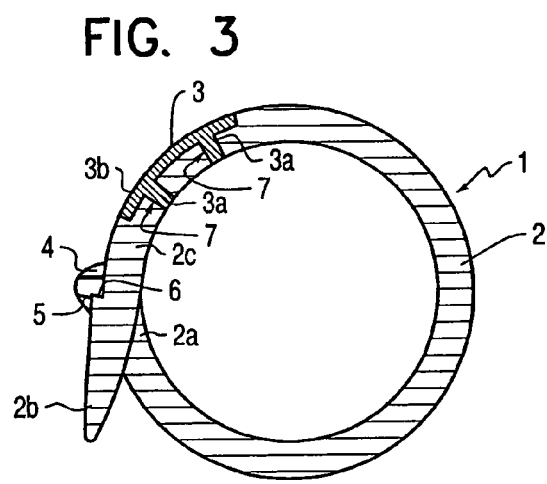
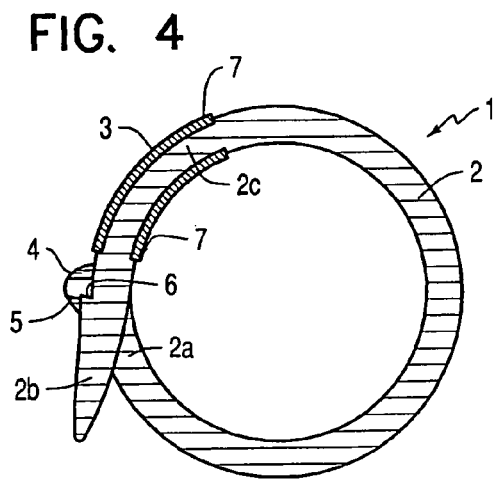
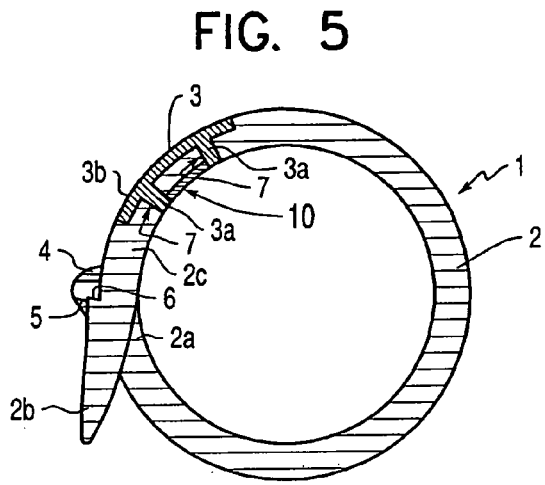

GASTRIC RING FOR TREATMENT OF OBESITY

CROSS-REFERENCE TO RELATED APPLICATIONS

This application is a continuation and claims the benefit of U.S. patent application Ser. No. 10/499,914 filed Aug. 11, 2004 now U.S. Pat. No. 7,297,103 which is a national stage application of PCT/FR03/00038 filed Jan. 8, 2003 which claims priority to French patent application No. 02.00260 filed Jan. 9, 2002. The entire content of each of these applications is incorporated by reference herein.

The present invention concerns a gastric ring for treatment of obesity. Such a ring is also presently known as a "gastroplasty ring".

It is known to treat a patient with pathological obesity by fitting a ring round the patient's stomach in such a way as to create, in the upper part of the stomach, a pouch of small dimensions, and an opening for flow of food, also of small dimensions.

The principle of such rings is well known, and the documents WO-A-86/04498 and EP-A-0 611 561 may be cited as documents illustrating existing gastric rings.

An existing gastric ring comprises an inflatable pouch situated on its inner face, making it possible to adjust the cross section of the opening delimited by the ring. This is because implantation of such a ring, which involves prior dissection, causes a greater or lesser degree of trauma to the stomach wall, and it is best not to immediately tighten this ring round this wall, so as to ensure that the latter can heal by scar formation.

The pouch is inflated by means of a fluid which is delivered percutaneously from an implantable chamber and by means of a conduit connecting this chamber to the pouch.

Some of the gastric rings according to the prior art have the disadvantage of being relatively aggressive with regard to the wall of the stomach, to the point of causing inflammation of this wall, or, in extreme cases, perforations of this wall. This aggressiveness is the result in particular of the pressure exerted by the inflatable pouch and of a lumen which is not perfectly continuous.

Moreover, said implantable chamber and said tube connecting this chamber and the pouch have the disadvantage of posing risks of leakage, migration and infection.

The chamber may be more or less visible beneath the skin, which is unfavorable from the esthetic point of view.

It is an object of the present invention to overcome all these disadvantages of the existing rings.

The ring to which the invention relates comprises in a manner known per se:
a band which is able to surround the wall of the stomach;
means for maintaining the band in the form of a ring able to surround the stomach, and
means with which it is possible, after implantation, to modify the cross section of the opening delimited by the ring.
According to the invention:
the band comprises at least one zone made of a material which is elastically deformable in the longitudinal direction of this band;
said zone has at least two bearing points formed on it at two locations separated in the longitudinal direction of the band, and
the ring comprises at least one rigid element made of a bioabsorbable or biodegradable material and bearing against said zone in the area of said bearing points, this rigid element, before absorption, making it possible to maintain said bearing points at a distance from one another different than the distance separating these two bearing points in the absence of elastic deformation of said zone of the band, and, after absorption, no longer forming an obstacle to the return of said zone of the band to its nondeformed state.

"Biodegradable" or "bioabsorbable" signifies the property by which a material degrades in vivo by a cellular, enzymatic or microbial mechanism (cf. for example degradation of collagen by collagenase) or by a physical-chemical mechanism (cf. for example hydrolysis of a lactic acid polymer).

Such a bioabsorbable material is preferably chosen from the group consisting of polymers of p-dioxanone, polyglycolides, polyorthoesters, polymers of trimethylene carbonate, stereocopolymers of L and D lactic acid, homopolymers of L lactic acid, copolymers of lactic acid and a compatible comonomer, such as alphahydroxy acid derivatives. Still more preferred, the bioabsorbable material has a polydispersity of less than 2.

By way of a preferred example, the biodegradable or bioabsorbable material is a lactic acid polymer (PLA) or polyglycolic acid polymer (PGA), or a copolymer of lactic acid or polyglycolic acid (PLA-PGA).

The ring according to the invention is placed round the stomach, after which the absorption of the element or elements made of bioabsorbable material which the ring comprises allows said deformable zone or zones of the band to recover their neutral form of nondeformation. The circumference of the ring, and thus the cross section of the opening delimited by this ring, can thus be adapted to the treatment needs of the patient.

This ring does not therefore comprise a pouch on its inner face, nor an implantable chamber and tube connecting this chamber to this pouch. The result of this is that the ring is largely nonaggressive with respect to the wall of the stomach and makes it possible to eliminate all the aforementioned disadvantages of using an inflatable pouch, implantable chamber and tube.

Each element made of bioabsorbable material is principally intended to maintain the zone of the band, along which it extends, in a stretched state; the ring can thus be put in place in a state of relative distension in order to permit cicatrization of the stomach wall, then, after absorption of its element or elements made of bioabsorbable material, undergo contraction as a result of the resilience of the material constituting said deformable zone.

The principles of the invention could however be applied inversely, in order to obtain a distension after absorption, in which case each element made of bioabsorbable material is intended to maintain the zone of the band, along which it extends, in a contracted state.

Preferably, the band forms, at one end, an eyelet delimiting a shoulder, and it has, at its other end, a tapered shape facilitating its insertion into the eyelet; this other end comprises at least one snap-fit catch intended to be snap-fitted into the eyelet and to cooperate with the shoulder in order to maintain the band in the form of a ring.

Said other end can comprise several successive catches, making it possible to close the band at several diameters adapted to the specific circumstances of the patient to be treated.

According to one possible embodiment of the invention:
each pair of bearing points is formed by two opposite zones of an opening formed radially and through said deformable zone of the band, this opening being of circular shape when the deformable zone is in a nondeformed state, but being able to assume an oblong shape when this deformable zone is stretched longitudinally; and each rigid element has an oblong tubular shape and is dimensioned so as to be able to be introduced with force into the aforementioned opening in order to confer on this opening a corresponding oblong shape, this oblong shape producing a correlated. longitudinal stretching of said deformable zone.

Each insert can have a slightly flared shape and can be placed on said deformable zone in such a way that its end of greater cross section is disposed on the outside of the ring.

This slightly flared shape permits adaptation of the insert to the curvature of the ring and thus avoids any risk of this insert being expelled when the band is curved to form the ring.

According to another possible embodiment of the invention:

each pair of bearing points is formed by two holes formed in said deformable zone of the band, and each rigid element has a staple shape, that is to say comprises a body having two stubs, these stubs being intended to be received in said holes; the distance separating the stubs is greater than the distance separating the two holes when said zone is in the unstretched state, so that the portion of this zone situated between these holes is stretched when these stubs are engaged in these holes.

The body of each element according to this other embodiment can have a curved shape permitting adaptation of this element to the curvature of the ring.

According to yet another possible embodiment of the invention:

each pair of bearing points is formed by two shoulders delimited by a portion with a cross section smaller than that of said deformable zone, and each rigid element has a tubular shape and is intended to be engaged on this portion of smaller cross section, in such a way as to bear against the shoulders, the length of this element being greater than the distance separating said shoulders when said deformable zone is in the unstretched state, in such a way that, when the ends of the tubular element are placed against these shoulders, said portion of smaller cross section is stretched.

The element can have a curved shape corresponding to the curvature of the ring, again to permit adaptation of this element to the curvature of the ring.

The invention will be clearly understood from the following description in which reference is made to the attached diagrammatic drawing which shows, by way of nonlimiting examples, three possible embodiments of the gastric ring in question.

FIGS. 1, 3 and 4 are views of this ring according to these three embodiments, respectively, shown in a cross section passing through the median plane of the thickness of this ring, and FIG. 2A is a partial view of the ring shown in FIG. 1, from the direction of the arrow A in FIG. 1; FIG. 2B is a partial view of one end of the band shown in FIG. 1, including several successive catches.

FIG. 5 is a further view of the ring, including a small plate that connects the stubs to one another.

To simplify matters, the elements or parts of elements found from one embodiment to another are designated by the same reference numbers.

FIG. 1 shows a gastric ring 1 used for treatment of pathological obesity of a patient and presently referred to as a "gastroplasty ring".

The ring 1 comprises a band 2 which is able to surround the stomach wall, and three rigid inserts 3.

The band 2 is made of a material which is elastically deformable in the longitudinal direction of this band and is in particular made of silicone. At one end 2a, it forms an eyelet 4 delimiting a shoulder 5. At its other end 2b, it has a tapered shape facilitating its insertion into the eyelet 4 and comprises a snap-fit catch 6 intended to be snap-fitted into the eyelet 4 and to cooperate with the shoulder 5 in order to maintain the band 2 in the form of a ring. As shown in FIG. 2B, end 2b can comprise several successive catches 6, making it possible to close the band 2 at several diameters adapted to the specific circumstances of the patient to be treated.

At its end 2b, the band 2 has a zone 2c in which three radial through-openings 7 are formed. Each opening 7 is circular when the band 2 is in a nondeformed state, but can assume an oblong shape when this zone 2c is stretched longitudinally.

Each insert 3 is made of a bioabsorbable or biodegradable material such as a lactic acid polymer (PLA) or polyglycolic acid polymer (PGA), or a copolymer of lactic acid or polyglycolic acid (PLA-PGA). As is shown in FIG. 2, it has an oblong tubular shape and is dimensioned in such a way as to be able to be introduced with force into an opening 7. It thus confers on this opening 7 a corresponding oblong shape which produces a correlated longitudinal stretching of the zone 2c.

To adapt to the curvature of the band 2 when the ends 2a and 2b are in engagement, the inserts 3 have a slightly flared shape, their ends of greater cross section being disposed on the outside of the ring 1.

In practice, the band 2 is introduced into the patient's body and placed round the stomach using a minimally invasive technique such as laparoscopy, after which the end 2b is engaged through the eyelet 4 until the catch 6 snap-fits behind the eyelet 4 and this catch 6 bears against the shoulder 5.

The respective locations of this catch 6 and of this shoulder 5 have been predetermined in such a way that the ring 1 thus formed has a relative distension in relation to the desired tightening of the stomach wall, so as to permit cicatrization of the stomach wall before exerting a tightening stress on this wall.

The thickness of the inserts 3 is calculated, as a function of the material used, to ensure mechanical rupture of these inserts 3 about one to two months after implantation, this rupture taking place under the combined effect of the absorption of the inserts 3 and the tension exerted by the band 2. The rupture of these inserts 3 allows the zone 2c to recover its neutral, unstretched state.

The ring 1 then undergoes contraction resulting from the resilience of the material constituting said zone 2c, which gives to the circumference of the ring 1, and thus to the cross section of the opening delimited by this ring 1, dimensions adapted to the treatment needs of the patient.

In the case of the ring 1 shown in FIG. 3, the zone 2c comprises two holes 7 which receive the stubs 3a of an inserted staple-shaped element 3. The distance separating the stubs 3a is greater than the distance separating the two holes 7 when zone 2c is in the unstretched state, so that the portion of this zone 2c situated between these holes 7 is stretched when these stubs 3a are engaged in these holes 7.

The body 3b of the element 3 which comprises the stubs 3a has a curved shape permitting adaptation of this element 3 to the curvature of the ring 1.

In the case of the ring 1 shown in FIG. 4, the zone 2c has a portion of smaller cross section forming two shoulders 7. A tubular element 3 is engaged on this portion of smaller cross section and bears against these shoulders 7. The length of the element 3 is greater than the distance separating the shoulders 7 when the zone 2c is in the unstretched state, so that, when the ends of the element 3 are placed against the shoulders 7, said portion of smaller cross section is stretched.

Here too, the element 3 has a curved shape corresponding to the curvature of the ring 1.

This gastric ring 1 affords a decisive improvement to the prior art, given that it does not comprise an inflatable pouch on its inner face, nor an implantable chamber and tube connecting this chamber to this pouch. The result is that this ring is largely nonaggressive with respect to the wall of the stomach and eliminates all the disadvantages associated with the use of an inflatable pouch, implantable chamber and tube.

It goes without saying that the invention is not limited to the embodiment described above by way of example, and that on the contrary it encompasses all variant embodiments falling within the scope of protection defined by the attached claims. Thus, the ring can comprise several deformable zones 2c; the band 2 can be of a monobloc structure, as shown, or can have, outside the zone or zones 2c, a structure different than that of this zone or these zones 2c; each element 3 is principally intended to maintain the corresponding zone 2c in a stretched state, but each zone 2c could be maintained in a contracted state by one or more of these elements 3 in order to obtain a distension of the ring after absorption of these elements 3; the element 3 can be in the form of a "staple" as shown in FIG. 3, but with stubs 3a having a length such that they traverse said deformable zone 2c and receive a small plate 10 engaged on them and connecting them to one another, this small plate 10 making it possible to distribute the forces exerted on these stubs 3a; these stubs 3a and this small plate 10 can be designed in such a way as to form an assembly, in particular by snap-fitting, between these stubs 3a and this small plate 10; so as not to form an excessive thickness on the inner face of the ring, the holes of the deformable zone 2c which are intended to receive said stubs 3a can be formed substantially perpendicular to the zone 2c, so as to be situated substantially parallel to the axis of the ring 1 after formation of the latter, such that the body 3b connecting these stubs 3a is situated on one axial side of the ring 1 and said small plate 10 on the other axial side of this ring 1.

The invention claimed is:

1. A gastric ring for treatment of obesity, comprising:
   an elongate band configured and dimensioned to surround the stomach of a patient, the band having, at one end portion thereof an eyelet and, at an opposite end portion, a snap fit catch for engaging the eyelet to hold the band in a ring shape around the stomach, the band including a deformable zone which is elastically deformable in the longitudinal direction of the band, the deformable zone defining a pair of bearing points separated longitudinally along the band; and
   at least two biodegradable rigid elements positioned in the deformable zone of the band adjacent the at least two bearing points, the rigid elements positioned such that the at least two bearing points are maintained at a distance less than the distance separating the two bearing points prior to degradation of the rigid elements, the band, when in position around the stomach of the patient, imparting substantially uniform, non-aggressive compression to the stomach to restrict stomach dimensions.

2. The gastric ring as claimed in claim 1, wherein the snap-fit catch includes a plurality of catches for engaging the eyelet to permit varying the diameter of the elongate band.

3. The gastric ring as claimed in claim 1, wherein each rigid element is made of a material selected from the group consisting of lactic acid polymer, polyglycolic acid polymer, copolymer of lactic acid and polyglycolic acid.

4. The gastric band as claimed in claim 1, wherein at least a portion of the deformable zone is formed of silicon.

5. The gastric ring as claimed in claim 1, wherein the elongate band is of unitary construction.

6. The gastric ring as claimed in claim 1, wherein the deformable zone includes at least two openings extending through the band, the at least two biodegradable rigid elements being positioned within the at least two openings to maintain a stretched configuration of the band.

7. The gastric ring as claimed in claim 6, wherein the material comprising the elongate band is biased towards an unstretched configuration such that the band returns to the unstretched configuration after degradation of the biodegradable rigid elements.

8. A gastric ring for treatment of obesity comprising:
   an elongate band configured and dimensioned to atraumatically surround the outer stomach wall of a patient to restrict the diameter of the stomach, the band having at one end thereof a first connector and, at the opposite end, a second connector, the first and second connectors being connectable to hold the band in a substantially ring shape around the stomach wall, the band including a deformable zone positioned between the first and second connector, the deformable zone being elastically deformable in the longitudinal direction of the band and defining at least two bearing points separated longitudinally along the deformable zone; and
   at least one biodegradable rigid element positioned at least in part adjacent the at least two bearing points, the rigid elements positioned such that the at least two bearing points are maintained at a distance different than the distance separating the two bearing points prior to degradation of the rigid element, the band, when positioned around the stomach wall of the patient, imparting substantially uniform non-aggressive compression to the stomach to restrict stomach dimensions.

9. The gastric ring as claimed in claim 8, wherein the first connector is an eyelet defined in an end portion of the band and the second connector is a catch formed in the opposite end of the band, the catch configured and dimensioned to be received within the eyelet.

10. The gastric ring as claimed in claim 9, wherein the catch is a snap-fit catch defining at least two successive catches that selectively close the band at different diameters.

11. The gastric ring as claimed in claim 8, wherein at least a portion of the deformable zone is formed of silicone.

12. The gastric ring as claimed in claim 8, wherein the rigid element, prior to degradation, maintains the deformable zone of the band in a stretched configuration to permit cicatrisation of the stomach wall and, after degradation of the rigid element, the band contracts to a predetermined diameter.

13. The gastric ring as claimed in claim 10, wherein each rigid element has a slightly flared shape such the each rigid element includes an end of lesser cross-section and an end of greater cross section, each rigid element being insertable in a respective opening of the deformable zone such that the end of greater cross section is disposed on the outside of the ring.

14. A gastric ring for treatment of obesity comprising:
   an elongate band configured and dimensioned to atraumatically surround the outer stomach wall of a patient to restrict the diameter of the stomach, the band having at one end thereof a first connector and, at the opposite end, a second connector, the first and second connectors being connectable to hold the band in a substantially ring shape around the stomach wall, the band including a deformable zone positioned between the first and second connector, the deformable zone being elastically deformable in the longitudinal direction of the band and defining at least two bearing points separated longitudinally along the deformable zone; and at least one biodegradable rigid element positioned at least in part adjacent the at least two bearing points, the rigid elements positioned such that the at least two bearing points are maintained at a distance different than the distance separating the two bearing points prior to degradation of the rigid element, the band, when positioned around the stomach wall of the patient, imparting substantially uniform non-aggressive compression to the stomach to restrict stomach dimensions, wherein each pair of bearing points is formed by two opposite zones of an opening formed radially and through the deformable zone of the band, the opening having a circular shape when the deformable zone is in a non-deformed state, and is deformed in an oblong shape when the deformable zone is stretched longitudinally; and each rigid element has an oblong tubular shape that press-fits into the opening to deform the opening into an oblong shape, and stretch the deformable zone in the longitudinal direction of the band.

15. A gastric ring for treatment of obesity comprising:

an elongate band configured and dimensioned to atraumatically surround the outer stomach wall of a patient to restrict the diameter of the stomach, the band having at one end thereof a first connector and, at the opposite end, a second connector, the first and second connectors being connectable to hold the band in a substantially ring shape around the stomach wall, the band including a deformable zone positioned between the first and second connector, the deformable zone being elastically deformable in the longitudinal direction of the band and defining at least two bearing points separated longitudinally along the deformable zone; and at least one biodegradable rigid element positioned at least in part adjacent the at least two bearing points, the rigid elements positioned such that the at least two bearing points are maintained at a distance different than the distance separating the two bearing points prior to degradation of the rigid element, the band, when positioned around the stomach wall of the patient, imparting substantially uniform non-aggressive compression to the stomach to restrict stomach dimensions, wherein each pair of bearing points is formed by two holes formed in the deformable zone of the band, and each rigid element has a staple shape, including a body having two stubs, the stubs being received in the holes, the distance separating the stubs being greater than the distance separating the two holes when the deformable zone is in an unstretched state, so that the portion of the deformable zone situated between the holes is stretched when the stubs are engaged in the holes.

16. The gastric ring as claimed in claim 15, wherein the body has a curved shape that adapts to the curvature of the ring.

17. The gastric ring as claimed in claim 16, wherein each pair of bearing points is formed by two shoulders delimited by a portion with a cross section smaller than that of the deformable zone, and each rigid element has a tubular shape engaged on the portion of smaller cross section, so as to bear against the shoulders, the length of the rigid element being greater than the distance separating the shoulders when the deformable zone is in the unstretched state, such that, when the ends of the tubular elements are bearing against the shoulders, the portion of smaller cross section is stretched in the direction of deformation of the band.

18. The gastric ring as claimed in claim 17, wherein the rigid element has a curved shape corresponding to the curvature of the ring.

19. A gastric ring for treatment of obesity, comprising:

a band extending along a longitudinal axis and being configured and dimensioned to surround a patient's stomach, the band including first and second ends with corresponding engagement structure such that the first and second ends are selectively engagable with one another to maintain the band in a ring shape around the stomach, the band being at least partially formed from a resilient material such that the band is elastically deformable along the longitudinal axis for repositioning between an unstretched configuration and a stretched configuration, the band being biased towards the unstretched configuration; and a rigid element engagable with the band to maintain the stretched configuration thereof; the rigid element being formed from a biodegradable material such that the band returns to the unstretched configuration upon degradation of the rigid element.

20. The gastric ring as claimed in claim 19, wherein the band is of unitary construction.

21. The gastric ring as claimed in claim 19, wherein the band is configured and dimensioned such that the first end at least partially overlaps the second end when the band is positioned about the stomach in the ring shape.

* * * * *